(12) United States Patent
Menendez et al.

(10) Patent No.: US 9,078,635 B2
(45) Date of Patent: Jul. 14, 2015

(54) ANTERIOR HIP REPLACEMENT RETRACTOR ASSEMBLY

(75) Inventors: Lawrence Richard Menendez, Manhattan Beach, CA (US); Daniel C. Allison, Studio City, CA (US); Daniel Bass, Half Moon Bay, CA (US); Bob Mastny, Palm Bay, FL (US); Terry Johnston, Redwood City, CA (US)

(73) Assignee: Tedan Surgical Innovations, LLC, Sugar Land, TX (US)

( * ) Notice: Subject to any disclaimer, the term of this patent is extended or adjusted under 35 U.S.C. 154(b) by 0 days.

(21) Appl. No.: 13/364,659

(22) Filed: Feb. 2, 2012

(65) Prior Publication Data
US 2013/0204091 A1 Aug. 8, 2013

(51) Int. Cl.
*A61B 1/32* (2006.01)
*A61B 17/02* (2006.01)
*A61B 19/00* (2006.01)

(52) U.S. Cl.
CPC ......... *A61B 17/02* (2013.01); *A61B 2017/0275* (2013.01); *A61B 2019/268* (2013.01)

(58) Field of Classification Search
CPC ............... A61B 17/02; A61B 17/0206; A61B 2019/268; A61B 2017/0275
USPC .................. 600/227–234; 403/384, 389–390, 403/217–219, 169–178
See application file for complete search history.

(56) References Cited

U.S. PATENT DOCUMENTS

| | | | | |
|---|---|---|---|---|
| 2,195,336 A | * | 3/1940 | Loop | 403/64 |
| 2,863,682 A | * | 12/1958 | Canepa | 403/175 |
| 3,509,873 A | * | 5/1970 | Karlin et al. | 600/226 |
| 3,810,462 A | | 5/1974 | Szpur | |
| 4,099,521 A | * | 7/1978 | Nestor et al. | 600/228 |
| 4,143,652 A | | 3/1979 | Meier et al. | |
| 4,617,916 A | | 10/1986 | LeVahn et al. | |
| 4,679,961 A | * | 7/1987 | Stewart | 403/341 |
| 4,718,151 A | * | 1/1988 | LeVahn et al. | 24/535 |
| 4,813,401 A | | 3/1989 | Grieshaber | |
| 4,867,404 A | | 9/1989 | Harrington et al. | |
| 4,949,707 A | * | 8/1990 | LeVahn et al. | 600/234 |
| 4,971,037 A | | 11/1990 | Pelta | |
| 4,993,862 A | * | 2/1991 | Pelta | 403/59 |

(Continued)

OTHER PUBLICATIONS

"StrongArm—Triple Arm", HelloTrade, retreived Mar. 28, 2013 <http:www.hellotrade.com/nvsurgical-products/strong-arm-triple-arm.html> 2 pages.*

(Continued)

*Primary Examiner* — Eduardo C Robert
*Assistant Examiner* — Jacqueline Johanas
(74) *Attorney, Agent, or Firm* — Kramer Amado P.C.

(57) ABSTRACT

A retractor assembly has a first clamp adapted to be mounted to a table, a first vertically oriented post supported by the clamp, a first main arm mounted for at least one of angular and lateral movement relative to the first post, and lockable in a selected position, and a tree assembly configured at one end of the second post. The tree assembly has at least two accessory arms, with each accessory arm having a first ball joint on a first end, and a pivot lock knob at an immediate portion, and each accessory arm having a second end configured to accept the mounting of a retractor to the accessory arm. The retractor assembly may also include a J-shaped hook mounted to a ratcheting linearly movable distractor assembly and trochanteric retractors mounted to the accessory arms for femoral elevation and exposure.

14 Claims, 6 Drawing Sheets

(56) References Cited

U.S. PATENT DOCUMENTS

| | | | |
|---|---|---|---|
| 5,025,780 A * | 6/1991 | Farley | 600/230 |
| 5,127,758 A * | 7/1992 | Kreusel | 403/171 |
| 5,704,900 A | 1/1998 | Dobrovolny et al. | |
| 5,902,233 A * | 5/1999 | Farley et al. | 600/213 |
| 6,085,749 A * | 7/2000 | Wardle et al. | 128/845 |
| 6,234,961 B1 | 5/2001 | Gray | |
| 6,302,843 B1 * | 10/2001 | Lees et al. | 600/228 |
| 6,315,718 B1 | 11/2001 | Sharratt | |
| 6,511,423 B2 | 1/2003 | Farley | |
| 6,626,830 B1 | 9/2003 | Califiore et al. | |
| 6,837,851 B1 * | 1/2005 | Valentini et al. | 600/210 |
| 6,856,828 B2 * | 2/2005 | Cossette et al. | 600/429 |
| 6,860,877 B1 | 3/2005 | Sanchez et al. | |
| 6,896,231 B1 * | 5/2005 | Sullivan | 248/311.2 |
| 7,125,380 B2 * | 10/2006 | Yager | 600/227 |
| 7,338,442 B2 | 3/2008 | Mulac et al. | |
| 7,458,933 B2 | 12/2008 | LeVahn et al. | |
| 7,611,460 B2 * | 11/2009 | Dobrovolny | 600/213 |
| 7,753,844 B2 | 7/2010 | Sharratt et al. | |
| 7,785,254 B2 * | 8/2010 | Teasdale | 600/228 |
| 2004/0002633 A1 * | 1/2004 | Phillips et al. | 600/228 |
| 2005/0113645 A1 * | 5/2005 | Sharratt et al. | 600/227 |
| 2005/0119697 A1 | 6/2005 | Sharratt | |
| 2005/0272982 A1 * | 12/2005 | Bjork et al. | 600/231 |
| 2006/0293568 A1 * | 12/2006 | Scheidegger-Pluss | 600/227 |
| 2006/0293569 A1 * | 12/2006 | Teasdale | 600/228 |
| 2007/0043266 A1 * | 2/2007 | Laucirica Gari | 600/228 |
| 2007/0093696 A1 | 4/2007 | Sharratt | |
| 2007/0158513 A1 * | 7/2007 | LeVahn et al. | 248/229.21 |
| 2007/0213597 A1 * | 9/2007 | Wooster | 600/234 |
| 2008/0154262 A1 * | 6/2008 | Brundobler et al. | 606/53 |
| 2008/0312509 A1 * | 12/2008 | Jacobson et al. | 600/230 |
| 2009/0287062 A1 * | 11/2009 | Farley | 600/231 |
| 2010/0192506 A1 * | 8/2010 | Allred et al. | 52/655.1 |
| 2011/0201897 A1 * | 8/2011 | Bertagnoli et al. | 600/229 |
| 2012/0035424 A1 * | 2/2012 | Schulte | 600/230 |
| 2012/0136215 A1 * | 5/2012 | Farley | 600/231 |
| 2013/0023735 A1 * | 1/2013 | Brown et al. | 600/229 |

OTHER PUBLICATIONS

Mediflex Surgical Products, "Surgical Holding & Positioning Arms", c. 2009, 3 pages.*

International Search report for PCT/US2013/024389, dated May 13, 2013.

* cited by examiner

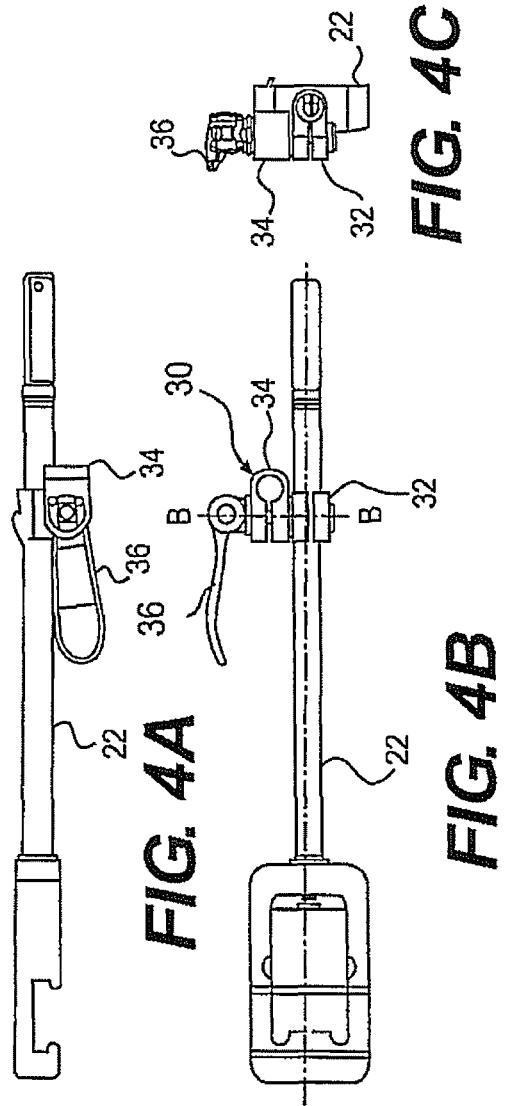

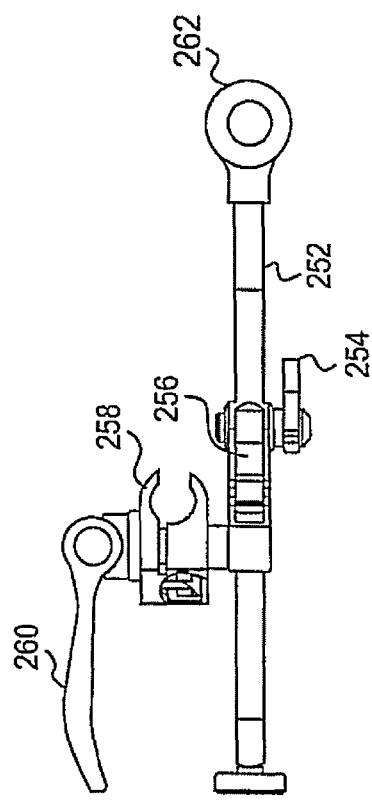
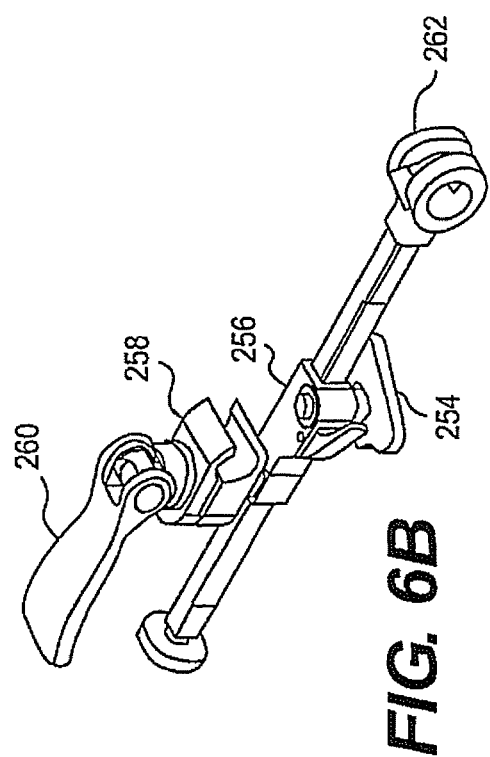
FIG. 6A
FIG. 6B

ANTERIOR HIP REPLACEMENT RETRACTOR ASSEMBLY

FIELD OF THE INVENTION

Some embodiments of the invention relate to the field of orthopedic surgery. Further, some embodiments of the invention relate to retractor assemblies that are used during surgery such as, for example, hip replacement surgery.

BACKGROUND OF THE INVENTION

Many types of surgery are performed on the human body, including hip replacement surgery. During such procedures, it is known to use the retractor assemblies in order to hold soft tissue in a position that permits the position to access the surgical area. In one common practice, a single retractor, or a number of retractors, will each be manually supported by an assistant. In these systems, the assistant will hold the retractor in position, and may apply a force against the soft tissue at the same time. In the case of relatively complex procedures such as hip replacement surgery, it may be necessary to use two or even a larger number of separate retractors, which may necessitate two or more assistants to manually operate the retractors. This may at some times be somewhat cumbersome.

SUMMARY OF THE INVENTION

A brief summary of various exemplary embodiments is presented. Some simplifications and omissions may be made in the following summary, which is intended to highlight and introduce some aspects of the various exemplary embodiments, but not to limit the scope of the invention. Detailed descriptions of a preferred exemplary embodiment adequate to allow those of ordinary skill in the art to make and use the inventive concepts will follow in later sections.

In various embodiments, a retractor assembly comprises: a first clamp adapted to be mounted to a table; a first vertically oriented post supported by the clamp; a first main arm mounted for at least one of angular and lateral movement relative to the first post, and lockable in a selected position; and a tree assembly configured at one end of the second post, the tree assembly comprising at least two accessory arms, with each accessory arm having a first ball joint on a first end thereof, and a pivot lock knob at an immediate portion thereof, and each accessory arm having a second end configured to accept the mounting of a respective retractor to the accessory arm.

In other various embodiments, a retractor assembly comprises: a first main post; a first main arm mounted to the first main post; a fitting disposed at one end of the first main arm; a first accessory arm operatively supported by the fitting and adopted to operatively support a first retractor; a second main arm mounted to the second main post; a second accessory arm operatively supported by the fitting and adopted to operatively support a second retractor; a third main arm mounted to the third main post; and a third accessory arm operatively supported by the fitting and adopted to operatively support a third retractor.

In alternative various embodiments, a retractor assembly comprises: a first main post a first main arm mounted to the first main post; a fitting disposed at one end of the first main arm; a first accessory arm operatively supported by the fitting and adopted to operatively support a first retractor; a second main arm mounted to the second main post; a second accessory arm operatively supported by the fitting and adopted to operatively support a second retractor; a third main arm mounted to the third main post; a third accessory arm operatively supported by the fitting and adopted to operatively support a third retractor; a second main arm mounted to the first main post; and a fourth accessory arm operatively mounted to the second main arm and adapted for supporting a retractor.

In still other alternative embodiments, a retractor assembly comprises: a second clamp adapted to be mounted to the table; a second vertically oriented post supported by the clamp; a third main arm mounted for at least one of angular and lateral movement relative to the second post, and lockable in a selected position; a J-shaped hook; and a distractor assembly movable linearly with respect to the third main arm, wherein the distractor is adapted to support the J-shaped hook.

The foregoing objects and advantages of the invention are illustrative of those that can be achieved by the various exemplary embodiments and are not intended to be exhaustive or limiting of the possible advantages which can be realized. Thus, these and other objects and advantages of the various exemplary embodiments will be apparent from the description herein or can be learned from practicing the various exemplary embodiments, both as embodied herein or as modified in view of any variation that may be apparent to those skilled in the art. Accordingly, the present invention resides in the novel methods, arrangements, combinations, and improvements herein shown and described in various exemplary embodiments.

BRIEF DESCRIPTION OF THE DRAWINGS

FIG. 4A is a side view of a subassembly of the assembly of FIG. 1.

FIG. 4B is a front view of the assembly of FIG. 4A.

FIG. 4C is an end view of the subassembly of FIG. 4A.

FIG. 6A is a side view of a subassembly of the assembly of FIG. 1.

FIG. 6B is a perspective view of the assembly of FIG. 6A.

DETAILED DESCRIPTION OF THE PREFERRED EMBODIMENTS OF THE INVENTION

Figure 2:
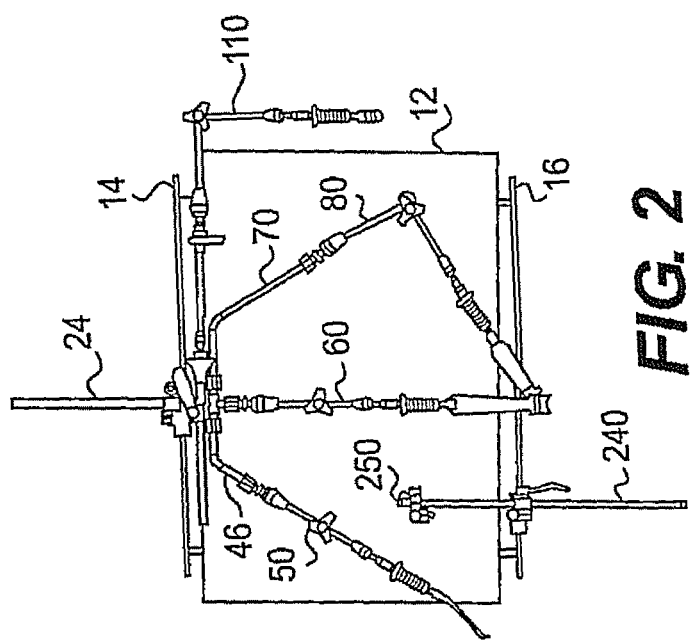
FIG. 2 is a top view of the assembly of FIG. 1.
Figure 3:
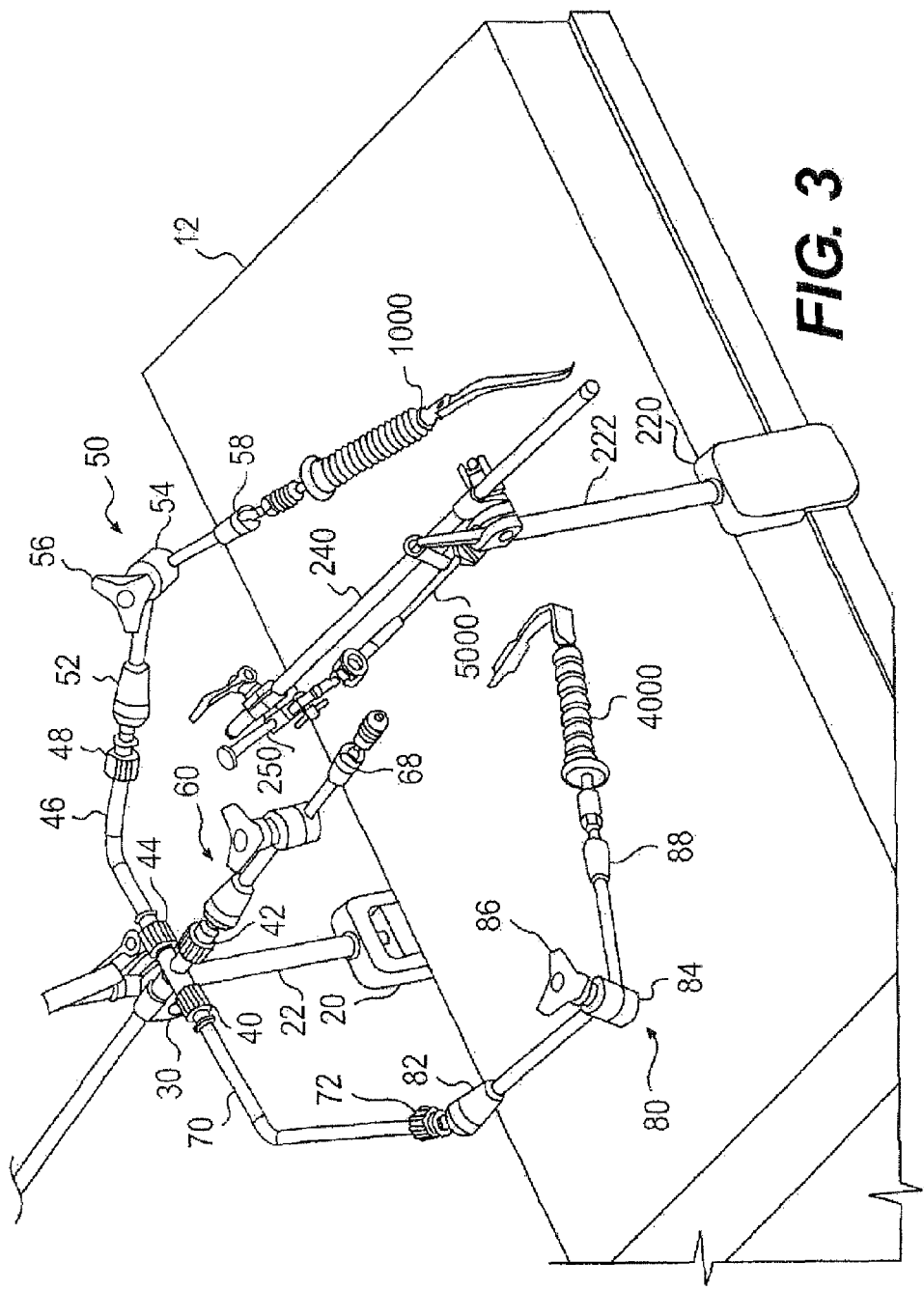
FIG. 3 is a perspective view of the assembly of FIG. 1, taken from a different angle.

Some embodiments of the invention will now be described with reference to the drawing figures, in which like reference numbers refer to like parts thereof. The following description refers to FIGS. 1 through 3 taken together, except that in some instances specific reference will be made to FIG. 4A through FIG. 6B.

A retractor assembly 10 is shown for use with an operating table 12. The operating table 12 is the only suitable table such as, for example, an orthopedic table which has a hinged portion to help position the patient. The patient is not illustrated, but can recline on the orthopedic table during surgery. The table 12 has longitudinal rails 14 and 16 as shown. These rails 14 and 16 provide a support for the retractor assembly.

A table clamp 20 is slidably mounted along the rail 14. The table clamp 20 supports a vertical side post 22. A T-post 24 is mounted to the post 22 on a clamp block 30.

FIGS. 4A and 4C show additional details of the post 22 and the clamp block 30. The clamp block 30 includes a first clamp 32 which can pivot around the post 22, slide longitudinal along the post 22, and also be fixed on the post 22. The clamp block 30 also has a second clamp 34 which can rotate around the axis B. A lever 36 is part of the second clamp 34, so that movement of the lever can compress the clamp block 30, thereby tightening it. The second clamp 34 holds a T-post 24 as will be described below.

Returning to FIGS. 1 through 3, a T-post 24 is supported by the clamp block 30 and can be moved longitudinally within the clamp block 30. The T-post 24 terminates in four quick connect ends 40, 42 and 44 respectively.

Figure 5A:
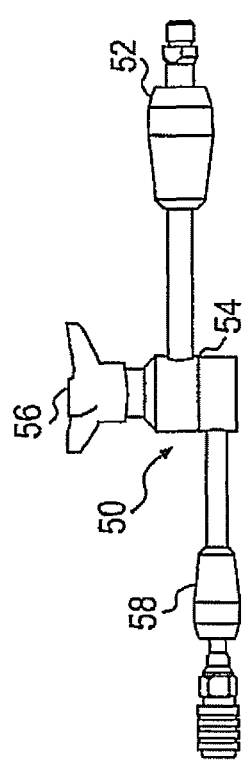
FIG. 5A is a side view of a subassembly of the assembly of FIG. 1.
Figure 5B:
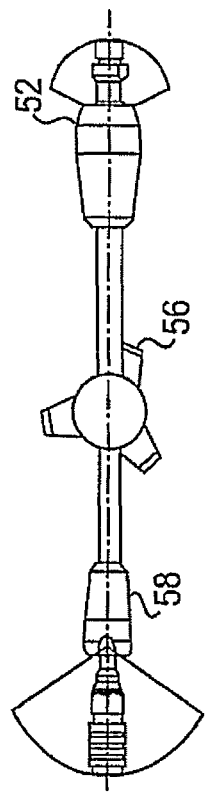
FIG. 5B is a front view of the assembly of FIG. 5A.
Figure 5C:
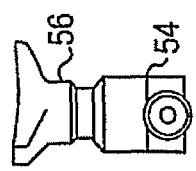
FIG. 5C is a side view of a subassembly of the assembly of FIG. 1.

Mounted to the quick connect 40 is a small fixed angle arm 46, which may be a non-straight extension arm. The small fixed angle arm 46 terminates on its own quick connect 48. Attached to the quick connect 48 is an accessory arm 50. FIGS. 5A through 5C show further details of an accessory arm 50. This illustration also corresponds to the components of the other accessory arms 60 and 80. Returning to FIGS. 1-3, the accessory arm 50 includes a connector 52, which connects to the quick connect 48, and which also has a ball and socket joint permitting a range of two-dimensional pivotal motion around the ball. The connector 52 may also include a ball and socket connection. Each ball and socket connection includes a tightening lockdown feature to fix it at a desired angle. The accessory arm 50 also has a pivot 54 which can be locked in position by a handle 56. The accessory arm 50 terminates in a connector 58 which also has a ball turn fitting. This connector 58 is adapted to receive a retractor, such as the illustrated straight hohmann retractor 1000.

Returning to the T-post 24, an accessory arm 60 is connected to the quick connect 42. This accessory arm 60 includes components 62, 64, 66 and 68 which correspond to items 52, 54, 56 and 58 described above. The accessory arm 64 thus supports a retractor 2000, such as the illustrated femur retractor 2000.

Returning to the T-post 24, connected to the quick connect 44 is a large fixed accessory arm 70, which may be a non-straight extension arm, that has at one end in its own quick connect 72, to which is connected another accessory arm 80. This accessory arm 60 includes components 62, 64, 66 and 68 which correspond to items 52, 54, 56 and 58 described above. The accessory arm 64 thus supports a retractor 2000, such as the illustrated femur retractor 2000.

Also supported on the post 22 by a clamp block 100 is an arm 102. The clamp block 100 is substantially similar in configuration to the clamp block 30. The arm 102 terminates at the ball joint 104 that supports an arm 106. A quick connect 108 leads to an accessory arm 110. The accessory arm 110 includes components 112, 114, 116 and 118 which correspond to components 52, 54, 56 and 58 as described above.

From the above, it will be appreciated that the above-described componentry provides for convenient positioning and locking of up to four retractors, 1000, 2000, 3000 and 4000. The wide range of degrees of freedom of are presented so that the retractors can be provisioned with a wide range of locations on the table at varying heights, and at varying spatial angles. Also the arm 102 may be attached to post 222 instead of post 22.

Retractor 1000 may be a straight hohmann retractor. Retractor 1000 may be used to retract soft tissue or bones. During various stages of an operation, retractor 1000 and/or similar retractors may be mounted to one or more accessory arms to provide constant exposure of the surgical site.

Retractor 2000 may be a two pronged stout trochanteric retractor. Retractor 2000 may be placed around the lesser trochanter of the femur. Retractor 2000 may be used to retract the proximal femur medially. Retractor 2000 may be secured to post 22 via accessory arm 60 and T-post 24 such that retractor 2000 comes from a direct medial location.

Retractor 3000 may be a smooth stout trochanteric retractor. Retractor 3000 may be placed around the greater trochanter of the femur. In various alternative embodiments, retractor 3000 may be a two pronged stout trochanteric retractor similar to retractor 2000. Retractor 3000 may be used to assist in femoral elevation. Retractor 3000 may be mounted to post 22 via accessory arm 80 and T-post 24 such that retractor 3000 comes from a posterior proximal location. In various alternative embodiments, retractor 3000 may be mounted to post 222 via an arm 102 and accessory arm 110. This alternative embodiment may allow retractor 3000 to be used from a lateral, posterior, proximal location.

Retractor 4000 may be an angled hohmann retractor. Retractor 4000 may be used to retract soft tissue or bones. During various stages of an operation, retractor 4000 and/or similar retractors may be mounted to one or more accessory arms to provide constant exposure of the surgical site.

Mounted to the rail 16 is a table clamp 220 which supports a vertical side post 222. A clamp block 230, similar to the clamp block 30, supports an arm 240. The arm 240 supports a ratcheting or rack and pinion femur distractor assembly 250, which is illustrated in more detail in FIGS. 6A and 6B. As shown in FIGS. 6A and 6B, the femur distractor 250 includes a rack 252 which can be laterally driven by a knob 254 having gear teeth, relative to a slider 256 which is mounted to a clamp 258 which grips the arm 240. A lever 260 compresses the clamp 258 to lock the distractor 250 onto the arm 240. Thus, the hook connection end 262 of the distractor 250 can be moved relative to the arm 240. Since the distractor 250 is arranged in the vertical configuration projecting down from the arm 240, it will be appreciated that rotation of the knob 254 can raise or lower the hook connection 262. The hook connection 262 is adapted to support in a swinging fashion a J-hook 5000. The J-hook 5000 is adapted to support the weight of a femur.

From the above it will be appreciated that the assembly provides a convenient method for positioning a femur J-hook and for mechanically raising and lowering the J-hook by turning a knob. A ratchet feature may also be incorporated along with or instead of the rack and pinion drive system.

J-hook 5000 may be adapted to be inserted around the proximal femur at a point just distal to the lesser trochanter. As described above, retractors 2000 and 3000 may be used to retract tissue and provide exposure and space for insertion of J-hook 5000. In various exemplary embodiments, J-hook 5000 may include a pointed tip that allows J-hook 5000 to pierce through the gluteus maximus tendon. J-hook 5000 includes a handle that may be used for holding the J-hook during insertion. The handle may also be used to pull the J-hook 5000 upwards toward distractor 250, where the J-hook 5000 may be attached at hook connection 262.

Figure 1:
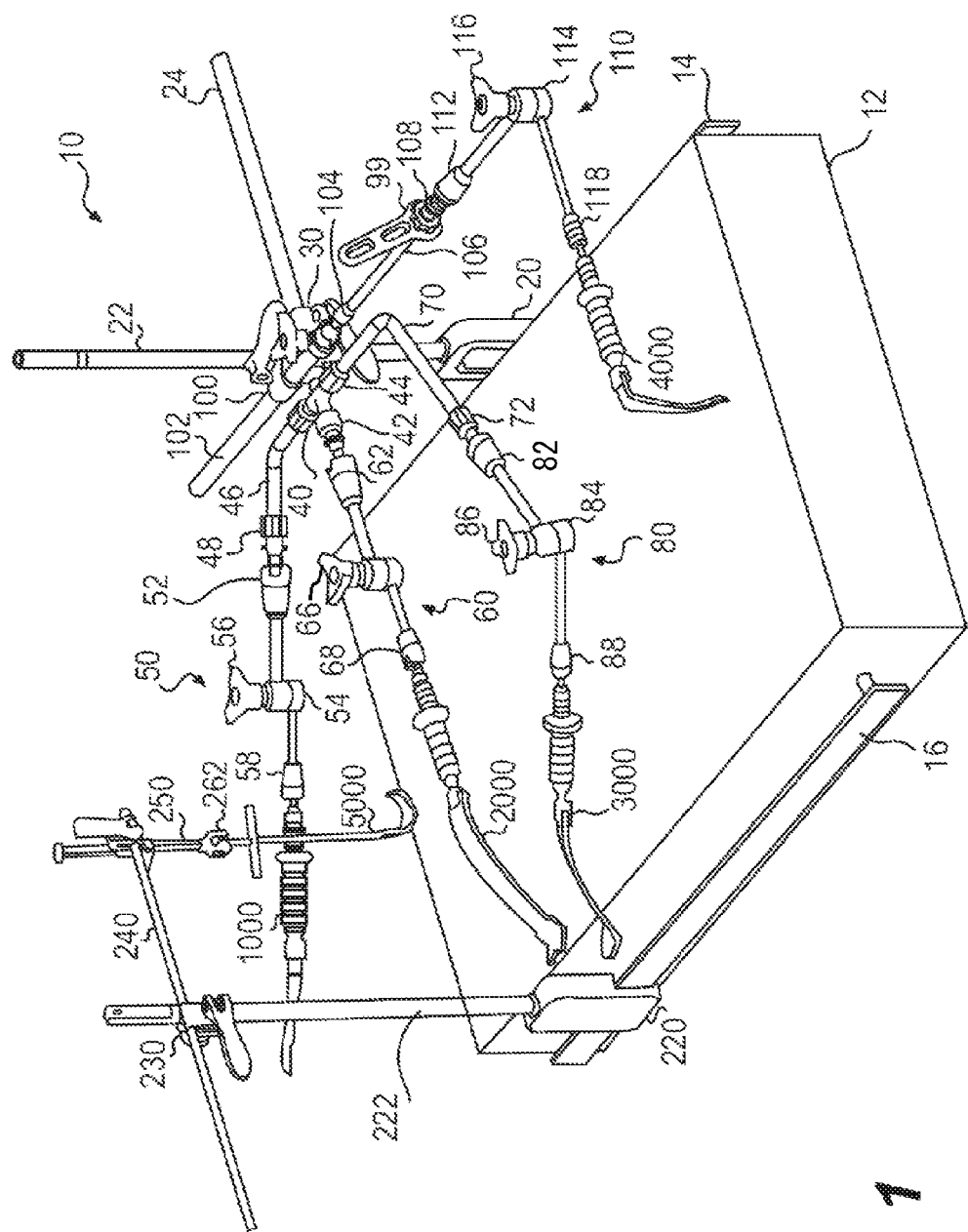
FIG. 1 is a perspective view of a retractor assembly according to a preferred embodiment.

FIG. 1 also depicts a wrench 99 which is a movable tool that can be used to secure or release the quick connects. The accessory arm 110 supports an angled hohmann and retractor 4000 as shown.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only and do not in any way limit the invention, which is defined only by the claims.

What is claimed is:

1. A retractor assembly comprising:
   a first clamp adapted to be mounted to a table;
   a first vertically oriented post supported by the clamp;
   a first main arm mounted for at least one of angular and lateral movement relative to the first post, and lockable in a selected position;
   a tree assembly configured at one end of the first main arm, the tree assembly comprising:
   a T-fitting;
   a fixed angle extension arm having a first end connected to the T-fitting by a first quick connect holder, and a second end connected to an accessory arm by a second quick connect holder; and,
   the accessory arm having a first end and a second end, the accessory arm having a first ball joint on the first end thereof, configured to engage the second quick connect holder, and the second end configured to receive a respective retractor to the accessory arm.

2. A retractor assembly according to claim 1,
   wherein the tree assembly comprises at least two fixed angle extension arms, each fixed angle extension arm having a respective first end connected to the T-fitting by a first quick connect holder and a second end connected by a second quick connect holder to a respective one accessory arm; and,
   a third accessory arm.

3. A retractor assembly according to claim 2, wherein T-fitting has three quick connect holders, each adapted to hold a respective accessory arm.

4. A retractor assembly according to claim 2, further comprising a second main arm mounted to the first post and mounted for at least one of angular movement and lateral movement with respect to the first post, the second main arm supporting a respective fourth accessory arm.

5. A retractor assembly according to claim 4, further comprising:
   a second clamp adapted to be mounted to the table;
   a second vertically oriented post supported by the clamp;
   a third main arm mounted for at least one of angular and lateral movement relative to the second post, and lockable in a selected position;
   a J-shaped hook having a pointed tip and a handle; and
   a distractor assembly movable linearly with respect to the third main arm, wherein the distractor is adapted to support the J-shaped hook.

6. A retractor assembly according to claim 1, wherein the accessory arm has a second ball joint at an opposite end from the first ball joint, and wherein the ball joints permit motion of the respective retractor with respect to the accessory arm.

7. A retractor assembly comprising:
   a first vertical main post;
   a first horizontal main arm mounted to the first vertical main post;
   a fitting disposed at one end of the first main arm;
   a first extension arm having a first end and second end, the first extension arm having a first quick connect holder mounted to the first end to connect the first extension arm to the fitting and a second quick connect holder mounted to the second end to facilitate connection to a first accessory arm;
   a first accessory arm having a first end and a second end, wherein the first end is configured to engage the second quick connect holder, and the second end is configured to connect a respective retractor to the first accessory arm;
   a second extension arm having a third quick connect holder to which a second accessory arm is attached;
   a second accessory arm having a first end configured to engage the third quick connect holder, and the second accessory arm having a second end configured to connect a respective retractor to the second accessory arm; and,
   a third accessory arm operatively supported by a third extension arm and adapted to operatively support a third retractor.

8. A retractor assembly according to claim 7, wherein the first accessory arm comprises two portions pivotable with respect to each other and a locking knob that locks the two portions in a selected angular position with respect to each other.

9. A retractor assembly according to claim 8, wherein the second accessory arm comprises two portions pivotable with respect to each other and a locking knob that locks the two portions in a selected angular position with respect to each other.

10. A retractor assembly according to claim 9, wherein the third accessory arm comprises two portions pivotable with respect to each other and a locking knob that locks the two portions in a selected angular position with respect to each other.

11. A retractor assembly comprising:
    a first vertical main post;
    a first main arm mounted perpendicular to the first main post via a clamp;
    a fitting disposed at one end of the first main arm and, the fitting having a first quick connect end, and a second quick connect end, and a third quick connect end;
    a first fixed angle extension arm connected to the fitting at a first end by a first quick connect holder and having a second quick connect holder at a second end configured to connect to a first accessory arm;
    a first accessory arm having a first end and a second end, the first accessory arm configured to engage the second quick connect holder of the first fixed angle extension arm, and the first accessory arm having a second end configured to receive a respective retractor to the first accessory arm;
    a second fixed angle extension arm connected to the fitting at a first end by a first quick connect holder and having a second quick connect holder at a second end configured to connect to a second accessory arm;
    a second accessory arm having a first end and a second end, the second accessory arm configured to engage the second quick connect holder of the second fixed angle extension arm at the first end, and configured to receive a retractor at the second end;
    a third accessory arm adapted to support a third retractor;
    a second main arm mounted to the first main post; and
    a fourth accessory arm operatively mounted to the second main arm and adapted for supporting a retractor.

12. A retractor assembly according to claim 11, wherein the first accessory arm comprises two portions pivotable with respect to each other and a locking knob that locks the two portions in a selected angular position with respect to each other.

13. A retractor assembly according to claim 11, wherein the second accessory arm comprises two portions pivotable with respect to each other and a locking knob that locks the two portions in a selected angular position with respect to each other.

14. A retractor assembly according to claim 11, wherein the third accessory arm comprises two portions pivotable with respect to each other and a locking knob that locks the two portions in a selected angular position with respect to each other.

\* \* \* \* \*